United States Patent

Nakano et al.

[11] Patent Number: 5,990,368
[45] Date of Patent: Nov. 23, 1999

[54] ISOMERIZATION OF ALLENES TO ALKYNES WITH AN ALKALINE-EARTH METAL HYDRIDE CONTAINING CATALYST

[75] Inventors: Mitsuru Nakano, Aichi, Japan; Bruce M. Novak, Amherst, Mass.

[73] Assignee: Kabushiki Kaisha Toyota Chuo Kenkyusho, Aichi, Japan

[21] Appl. No.: 09/111,365

[22] Filed: Jul. 7, 1998

[51] Int. Cl.⁶ .................... C07C 2/00; C07C 2/02; C07C 5/23
[52] U.S. Cl. .................... 585/538; 585/534; 585/664; 585/665; 585/666; 585/667; 585/668; 585/669; 585/670
[58] Field of Search .................... 585/538, 534, 585/664, 665, 666, 667, 668, 669, 670

[56] References Cited

U.S. PATENT DOCUMENTS

| | | | |
|---|---|---|---|
| 2,594,706 | 4/1952 | Allan | 585/538 |
| 3,235,618 | 2/1966 | Hastings et al. | 585/538 |
| 3,369,054 | 2/1968 | Zelinski et al. | 585/538 |
| 3,671,605 | 6/1972 | Smith, Jr. | 585/538 |
| 4,036,904 | 7/1977 | Strope | 585/538 |
| 5,062,998 | 11/1991 | Herman et al. | 585/538 |

FOREIGN PATENT DOCUMENTS

| | | |
|---|---|---|
| 47-38593 | 12/1972 | Japan . |
| 4-225987 | 8/1992 | Japan . |

*Primary Examiner*—Walter D. Griffin
*Assistant Examiner*—In Suk Bullock
*Attorney, Agent, or Firm*—Oblon, Spivak, McClelland, Maier & Neustadt, P.C.

[57] ABSTRACT

Providing an isomerization process which can isomerize allenes to alkynes less expensively and stably is an assignment to be solved by the present invention and given thereto. The present invention is an isomerization process including the step of reacting an allene-lype hydrocarbon compound $(R_1R_2C=C=CR_3R_4)$ in the presence of alkaline-earth metal hydride working as an isomerization catalyst, thereby isomerizing the allene-type hydrocarbon compound to an alkyne-type hydrocarbon compound $(R_1C\equiv C-CR_2R_3R_4)$.

6 Claims, No Drawings

ISOMERIZATION OF ALLENES TO ALKYNES WITH AN ALKALINE-EARTH METAL HYDRIDE CONTAINING CATALYST

BACKGROUND OF THE INVENTION

1. Field of the Invention

The present invention relates to a process for isomerizing allenes to alkynes.

2. Description of the Related Arts

As for a conventional process for isomerizing an acetylene-type compound to an allene-type compoun, there has been a disclosure, for example, Japanese Unexamined Patent Publication (KOKAI) No. 47-38,593, on a conventional isomerization process which is processed by using metallic ruthenium as a catalyst at room temperature in order to alternately isomerize the acetylene-type compound and the allene-type compound. Moreover, there has been another disclosure, for example, Japanese Unexamined Patent Publication (KOKAI) No. 4-225,987, on another conventional isoinerization process in which an allene-type hydrocarbon compound is isomerized to produce metallized 1-alkyne by using a mixture of alkylamine and alkali metal hydride as an isomerization catalyst in the presence of alkali metal.

It has been revealed recently that mixtures of allenes, such as $CH_2=C=CH_2$, and alkynes, such as $HC\equiv C-CH_3$, give copolymers (or reactive elastomers) by organometallic catalysts represented by Ni complexes. In the laboratory level synthesis, it is possible to obtain both allene and propyne in their pure forms, and to control the compositional ratios of the resultant copolymers by mixing them in arbitrary ratios. However, it is quite difficult to separate them in a large scale because their physical properties, such as a boiling point, are very close (see allene (bp. $-32°$ C.), propyne (bp. $-23°$ C.).).

The MAPP gas has been known, and is commercially available as a material supply source of allene/propyne. The MAPP gas contains allene in an amount of from 18 to 28% by weight, propyne in an amount of from 23 to 36% by weight, and propylene and butane in an amount of from 1 to 8% by weight. However, it is difficult to adjust the composition of the MAPP gas at a desired compositional ratio. Therefore, the conventional technique, in which the metallic ruthenium is used as a catalyst, is not proper industrially, because the isomerization reaction is carried out by utilizing the thermodynamic equilibrium. Accordingly, the isomerization reaction develops slow. Further, the publication does not set forth on how to control the isomerization reaction. Consequently, there arises a drawback in that the composition ratio cannot be selected. Furthermore, there is another problem in that the expensive metallic ruthenium is used as a catalyst.

When the allenes and alkynes are used as monomers for polymerization, it is essential to employ a step of drying the monomers. This is because the organometallic compounds, which are prepared from transition metals, are used as a catalyst. However, it is impossible to isomerize and dry the allenes and alkynes at the same time.

In the latter process, drying is not effective during the isomerization reaction. Moreover, when carrying out the allene/alkyne polymerization by using the resulting isomerized product, there arises a drawback in that the alkylamine contained in the isomerization catalyst poisons the polymerization catalysts.

It is an assignment to be solved by the present invention and given thereto to provide a process which can isomerize allenes to alkynes less expensively and stably.

SUMMARY OF THE INVENTION

As measures to solve the assignment, the inventors of the present invention devised the following aspects of the present invention as hereinafter described.

In an aspect of the present invention, an isomerization process according to the present invention comprises the step of:

reacting an allene-type hydrocarbon compound ($R_1R_2C=C=CR_3R_4$) in the presence of alkaline-earth metal hydride working as an isomerization catalyst, thereby isomerizing the allene-type hydrocarbon compound to an alkyne-type hydrocarbon compound ($R_1C\equiv C-CR_2R_3R_4$).

In this aspect of the present invention, the allene-type hydrocarbon compound can be expressed by a general formula $R_1R_2C=C=CR_3R_4$, and the alkyne-type hydrocarbon compound cam be expressed by a general formula $R_1C\equiv C-CR_2R_3R_4$. Here, $R_1$, $R_2$, $R_3$ and $R_4$ can be at least one member selected from the group consisting of hydrogen, an alkyl group, halogen and an acyl group. The allene-type hydrocarbon compound can be allene, methylallene, ethylallene, dimethylallene, etc. In particular, it is preferred to use allene (i.e., $R_1=R_2=R_3=R_4=H$). On the other hand, as expressed by the general formula, the alkyne-type hydrocarbon compound is isomerized from the allene-type hydrocarbon compound by isomerizing the double bonds of the allene-type hydrocarbon compound into the triple bond (i.e., an acetylene-based compound). The positions of the substituent groups are the same as those of the allene-type hydrocarbon compound. Hence, both of the compounds exhibit similar properties with each other.

The alkaline-earth metal hydride can be used as the isomerization catalyst in the present invention. The alkaline-earth metal hydride can be beryllium hydride, magnesium hydride, calcium hydride, strontium hydride, barium hydride, etc. In particular, it is preferred to use calcium hydride.

The isomerization reaction is carried out by bringing a raw material containing the allene-type hydrocarbon into contact with the alkaline-earth metal hydride working as the isomerization catalyst. As for the reaction temperature of the isomerization, the isomerization reaction can preferably be carried out, for example, at a temperature of $-20°$ C. or more because allene is a gas. It is most preferred to carry out the isomerization reaction at around room temperature in view of operating the reaction. Moreover, in order to facilitate the isomerization reaction of the allene-type hydrocarbon compound having substituent groups, it is possible to isomerize it under a heated condition, for instance, at $50°$ C. In addition, when the isomerization reaction is carried out by heating, it is preferred to carry out the reaction in a pressure resistant container because the alkynes and allenes described here are mainly gases.

In the isomerization reaction, it is possible to control the isomerization degree of the allenes by appropriately selecting the reaction temperature and the contacting time with the catalyst. The isomerization reaction usually develops fast at room temperature. However, even if there exists calcium hydride, it is possible to completely suppress the isomerization, for example, at $-78°$ C.

The alkaline-earth metal hydride also works as a dehydration agent to the alkynes and allenes. When it is brought into contact with the alkynes and allenes at a temperature of $-40°$ C. compound below, it is possible to suppress the isomerization reaction, but to exclusively develop the drying step.

When a mixture of the alkynes and allenes is employed for the copolymerization catalyzed by organometallic compounds (e.g., Ni complexes), it is essential to dry both allenes and alkynes. When the drying is carried out insufficiently, the cross-linking reaction occurs during the polymerization so that only the insoluble and unmeltable products are obtained. However, in accordance with the aforementioned processing or isomerization reaction, the isomerization and drying can be carried out in a single step, because the dehydration is carried out simultaneously when the reactants are brought into contact with the present isomerization catalyst. Accordingly, it is possible to develop the polymerization without deteriorating the activity of the polymerization catalysts (e.g., Ni complexes). As a result, it is possible to readily produce copolymers having desired compositional ratios, copolymers which include the isomerized alkynes and allenes. In other words, it is possible to obtain an allene/alkyne (especially, propyne) mixture gas having an arbitrary composition in a fully dried state.

By applying the present process, it is possible to readily obtain monomers which can produce the following useful polymers.

The alkynes can be also used independently as monomers for producing acetylene-based polymers.

Monomers for Allene/Propyne Copolymers (Reactive Elastomers)

The allene/propyne copolymers are low-temperature elastomers which have structures similar to that of polybutadiene. In accordance with the present isomerization process, the monomers can be formed to have desired compositional ratios, and copolymers can be prepared to have compositions which are based on the isomerization. The resulting copolymers are different from polybutadiene, and are characterized in that they have two kinds of double bonds whose reactivities differ from each other. It is possible to readily prepare copolymers of different compositions by freely controlling the isomerization of allene/propyne mixture gases of the monomers.

Monomers for Conductive Polymers

The present isomerization process can produce propyne which is substantially pure. Polypropyne is a polymer which has alternate double bonds. The polymer exhibits an intermediate conductivity. However, when it is copolymerized with acetylene, it is possible to prepare conductive films which have film-forming abilities.

Monomers for Synthesizing Oxygen-Enrichment Films

Pure propyne is also an important precursor for a considerable number of substituted alkynes. Recently, the polymers of substituted alkynes have been expanding the applications. In particular, poly(1-trimethylsilyl-1-propyne) is an excellent material which exhibits the maximum oxygen permeability in all of polymers. 1-trimethylsilyl-1-propyne, the monomer of poly(1-trimethylsilyl-1-propyne), has been known to be synthesized by employing propyne as a raw material. Propyne can be prepared by using the catalyst of the present isomerization process. Accordingly, the present isomerization process is a very effective way for supplying propyne from the allene/propyne mixture gases less expensively and with ease.

DETAILED DESCRIPTION OF THE PREFERRED EMBODIMENTS

First Preferred Embodiment 100 g of a mixture gas including allene in an amount of 60% by weight and propyne in an amount of 40% by weight was introduced into a pressure resistant bottle, in which calcium hydride was held in an amount of 10 g, and was stirred at 30° C. for 1 hour. After the stirring, the composition of the mixture gas was determined by the NMR analysis, and was found that the mixture gas included allene in an amount of 12% by weight and propyne in an amount of 88% by weight. Therefore, allene was isomerized to propyne so that the content was decreased from 60% by weight to 12% by weight. On the contrary, the content of propyne was increased from 40% by weight to 80% by weight. Thus, it was verified that the isomerization reaction developed rapidly.

An allene/propyne copolymer could be made from the resulting mixture gas by using an Ni-complex catalyst. In the polymerization reaction, no desired copolymer could be produced when the monomers were not fully dried. However, the copolymer prepared by the present process was meltable, and was soluble to organic solvents, such as toluene, chloroform and tetrahydrofuran.

Second Preferred Embodiment 100 g of a mixture gas including allene in an amount of 60% by weight and propyne in an amount of 40% by weight was introduced into a pressure resistant bottle, in which calcium hydride was held in an amount of 10 g, and was stirred at −20° C. for 1 hour. After the stirring, the composition of the mixture gas was determined by the NMR analysis, and was found that the mixture gas included allene in an amount of 45% by weight and propyne in an amount of 55% by weight. Therefore, allene was isomerized to propyne so that the content was decreased from 60% by weight to 45% by weight. On the contrary, the content of propyne was increased from 40% by weight to 55% by weight. Thus, it was verified that the isomerization reaction developed rapidly.

An allene/propyne copolymer could be made from the resulting mixture gas by using an Ni-complex catalyst.

Third Preferred Embodiment 100 g of a mixture gas including allene in an amount of 60% by weight and propyne in an amount of 40% by weight was introduced into a pressure resistant bottle, in which calcium hydride was held in an amount of 10 g, and was stirred at 30° C. for 8 hours. After the stirring, the composition of the mixture gas was determined by the NMR analysis, and was found that the mixture gas included allene in an amount of 4% by weight and propyne in an amount of 96% by weight. Therefore, allene was isomerized to propyne so that the content was decreased from 60% by weight to 4% by weight. On the contrary, the content of propyne was increased from 40% by weight to 96% by weight. Thus, it was verified that the isomerization reaction developed rapidly.

An allene/propyne copolymer could be made from the resulting mixture gas by using an Ni-complex catalyst.

Comparative Example 100 g of a mixture gas including allene in an amount of 60% by weight and propyne in an amount of 40% by weight was introduced into a pressure resistant bottle, in which calcium hydride was held in an amount of 10 g, and was stirred at −78° C. for 24 hours. After the stirring, the composition of the mixture gas was determined by the NMR analysis, and was found that the mixture gas included allene in an amount of 60% by weight and propyne in an amount of 40% by weight. Thus, it was verified that no isomerization reaction developed.

Fourth Preferred Embodiment 100 g of a mixture gas including allene in an amount of 60% by weight and propyne in an amount of 40% by weight was introduced into a pressure resistant bottle, in which calcium hydride was held in an amount of 10 g, and was stirred at 45° C. for 15 minutes. After the stirring, the composition of the mixture gas was determined by the NMR analysis, and was found that the mixture gas included allene in an amount of 7% by weight and propyne in an amount of 93% by weight. Therefore, allene was isomerized to propyne so that the content was decreased from 60% by weight to 7% by weight. On the contrary, the content of propyne was increased from 40% by weight to 93% by weight. Thus, it was verified that the isomerization reaction developed rapidly.

An allene/propyne copolymer could be made from the resulting mixture gas by using an Ni-complex catalyst.

Dehydration Effect of the Present Catalyst

Toluene was refluxed in the presence of metallic sodium and benzophenone to dehydrate so that $H_2O<1$ ppm. An allene/propyne mixture gas, which was dried by the present isomerization process, was introduced into and dissolved into the dehydrated toluene. The liquid color (purplish red) of the toluene specifying the dryness did not vary at all. Thus, it was found that the allene/propyne mixture gas was in an extremely dried state. On the other hand, when an allene/propyne mixture gas was introduced into the toluene without bringing it into contact with the calcium hydride, the toluene changed its color from purplish red to light green. Thus, it was found that the allene/propyne mixture gas was dried insufficiently.

When the solvent, such as toluene, is admixed and refluxed with sodium/benzophenone, the mixture usually changes its color as follows as the drying proceeds: light green→green→bluish green→bluish purple→purplish red. When the mixture is put into the bluish purple or purplish red state, it is judged to be in a fully dried state (e.g., $H_2O<1$ ppm).

What is claimed is:

1. An isomerization process, comprising the step of: reacting an allene-type hydrocarbon compound in the presence of an isomerization catalyst including alkaline-earth metal hydride, thereby isomerizing the allene-type hydrocarbon compound to an alkyne hydrocarbon compound, wherein said allene-type hydrocarbon compound is $R_1R_2C=C=CR_3R_4$ wherein $R_1$, $R_2$, $R_3$ and $R_4$ are at least one member selected from the group consisting of hydrogen, alkyl, halogen and acyl.

2. The isomerization process according to claim 1, wherein said alkaline-earth metal hydride is at least one member selected from the group consisting of beryllium hydride, magnesium hydride, calcium hydride, strontium hydride and barium hydride.

3. The isomerization process according to claim 2, wherein said alkaline-earth metal hydride is calcium hydride.

4. The isomerization process according to claim 1, wherein said alkyne hydrocarbon compound is $R_1C\equiv C-CR_2R_3R_4$ in which $R_1$, $R_2$, $R_3$ and $R_4$ are at least one member selected from the group consisting of hydrogen, alkyl, halogen and acyl.

5. The isomerization process according to claim 1, wherein said allene-type hydrocarbon is at least one member selected from the group consisting of allene, methylallene, ethylallene and dimethylallene.

6. The isomerization process according to claim 1, wherein said isomerization reaction is carried out at a temperature of −20° C. compound more.

* * * * *